United States Patent
Reder et al.

(10) Patent No.: US 11,304,956 B2
(45) Date of Patent: Apr. 19, 2022

(54) USE OF 7-BROMO-5-(O-CHLOROPHENYL)-3-PROPOXY-1,2-DIHYDRO-3H-1,4-BENZODIAZEPIN-2-ONE FOR INHIBITION OF NEUROPATHIC PAIN AND SEIZURES OF DIFFERENT ETIOLOGY

(71) Applicants: Anatoliy Semenovich Reder, Odessa (UA); Dmytro Volodymyrovich Pozigun, Odessa (UA)

(72) Inventors: Anatoly Semenovich Reder, Odessa (UA); Sergey Andreevich Adronati, Odessa (UA); Mykola Yakovich Golovenko, Odessa (UA); Viktor Ivanovich Pavlovskiy, Odessa (UA); Tatiyana Anatolyevna Kabanova, Odessa (UA); Olena Igorivna Khalimova, Odessa (UA); Vitaly Borysovich Larionov, Odessa (UA); Natalia Ivanivna Voloshchuk, Vinnitsa (UA)

(73) Assignees: Anatoly Semenovich Reder, Odessa (UA); Dmytro Volodymyrovich Pozigun, Odessa (UA)

( * ) Notice: Subject to any disclaimer, the term of this patent is extended or adjusted under 35 U.S.C. 154(b) by 233 days.

(21) Appl. No.: 16/338,902

(22) PCT Filed: Oct. 26, 2017

(86) PCT No.: PCT/UA2017/000102
§ 371 (c)(1),
(2) Date: Apr. 2, 2019

(87) PCT Pub. No.: WO2018/067102
PCT Pub. Date: Apr. 12, 2018

(65) Prior Publication Data
US 2021/0169895 A1    Jun. 10, 2021

(30) Foreign Application Priority Data
Oct. 3, 2016  (UA) .............................. A 2016 10083

(51) Int. Cl.
A61K 31/5513    (2006.01)
A61P 23/00      (2006.01)
A61P 25/08      (2006.01)
A61P 29/00      (2006.01)
A61K 9/00       (2006.01)

(52) U.S. Cl.
CPC ........ *A61K 31/5513* (2013.01); *A61K 9/0053* (2013.01); *A61P 23/00* (2018.01); *A61P 25/08* (2018.01); *A61P 29/00* (2018.01)

(58) Field of Classification Search
CPC ... A61K 31/5513; A61K 9/0053; A61P 23/00; A61P 25/08; A61P 29/00
See application file for complete search history.

(56) References Cited

FOREIGN PATENT DOCUMENTS

| UA | 108246 C2 | 4/2015 | |
|----|-----------|--------|---|
| WO | WO-2003051275 A2 * | 6/2003 | |
| WO | WO-2020131000 A1 * | 6/2020 | ............. A61P 25/02 |

OTHER PUBLICATIONS

Gabra; Biol. Chem. 2006, 387, 127-143. (Year: 2006).*
Galluzzi; The Journal of the American Osteopathic Association, 2005, 105, S12-S19. (Year: 2005).*
Wood; J. Med. Chem. 2003, 46, 10, 1803-1806. (Year: 2003).*
Andronati; Eur. J. Med. Chem. 2010, 45, 1346-1351. (Year: 2010).*
Pavlovsky; Pharmaceutical Chemistry Journal 2012, 46, 540-545. (Year: 2012).*
Pavlovsky et al., "Analgesic Effects of 3-Substituted Derivatives of 1,4-Benzodiazepines and their Possible Mechanisms". Neurophysiology vol. 45, pp. 427-432, 2013.
Pavlovsky et al., "Analgesic and Anti-Inflammatory Properties of the Novel 3-Alkoxy-1,2-Dihydro-3H-1,4-Benzodiazepin-2-Ones", Odesa National University Herald, vol. 18, No. 3(47), 2013.
International Search Report and Written Opinion in related PCT Application No. PCT/UA2017/000102, dated Jan. 10, 2018 (8 pages).

* cited by examiner

*Primary Examiner* — Daniel R Carcanague
(74) *Attorney, Agent, or Firm* — Lathrop GPM LLP; Brian C. Trinque

(57) ABSTRACT

The invention relates to medical chemistry, in particular to the use of 7-bromo-5-(o-chlorophenyl)-3-propoxy-1,2-dihydro-3H-1,4-benzodiazepin-2-one as a drug which inhibits neuropathic pain without the formation of defects in the gastric mucosa (ulcerogenic effect), and possesses an anticonvulsant property.

4 Claims, No Drawings

USE OF 7-BROMO-5-(O-CHLOROPHENYL)-3-PROPOXY-1,2-DIHYDRO-3H-1,4-BENZODIAZEPIN-2-ONE FOR INHIBITION OF NEUROPATHIC PAIN AND SEIZURES OF DIFFERENT ETIOLOGY

RELATED APPLICATIONS

This application is a 35 U.S.C. § 371 filing of International Application No. PCT/UA2017/000102, filed Oct. 26, 2017, which claims the benefit of Ukraine Patent Application No. a201610083, filed Oct. 3, 2016. The entire contents of these applications are incorporated herein by reference in their entireties.

The invention relates to medical chemistry, in particular to the use of 7-bromo-5-(o-chlorophenyl)-3-propoxy-1,2-dihydro-3H-1,4-benzodiazepin-2-one (1) for the inhibition of neuropathic pain without damage of the gastric mucosa (ulcerogenic effect) and some convulsions caused by chemical agents and electrostimulation.

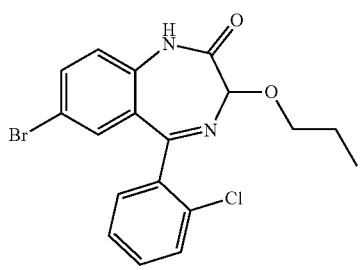

The International Association for the Study of Pain (IASP) defines neuropathic pain (NP) as pain "caused by primary damage or dysfunction of the nervous system" (see Lau F H, Chung K C. Silas Weir Mitchell, M D: the physician who discovered causalgia. J Hand Surg. 2004; 29, pp. 181-187). According to estimates, millions of people are afflicted with NP, although exact figures are currently unavailable. Most of common diseases, injuries or interventions cause NP by damaging somatosensory pathways in the peripheral or central nervous system. NP refers to chronic pain unlike acute-nociceptive. The main factors leading to the emergence of NP include diabetes mellitus, herpetic infection, stroke, multiple sclerosis, malignant diseases, HIV infection, as well as post-traumatic and postoperative damage to the peripheral nervous system (see James N. Campbell, Richard A. Meyer. Mechanisms of Neuropathic Pain. Neuron. 2006 Oct. 5; 52(1): pp. 77-92). For pharmacotherapy of NP, local anesthetics, opioids, central muscle relaxants, antiarrhythmic agents, antidepressants and anticonvulsants are used. Among NSAIDs, in some cases, ketorolac is used. However, frequent side effects limit the use of these drugs (see Danilov A. B., Davyidov O. S. Neuropathic pain. Moscow: Borges, 2007. 198p.; Attal N., Cruccu G., Haanpaa M., Hansson P., Jensen T. S., Nurmikko T., Sampaio C., Sindrup S., Wiffen P. EFNS guidelines on pharmacological treatment of neuropathic pain. European Journal of Neurology 2006, 13:1153-1169).

Earlier we synthesized a series of 3-alkoxy-1,2-dihydro-3H-1,4-benzodiazepin-2-ones derivatives (see Pavlovskyi V. I., Kabanova T. A., Khalimova O. I., Ushakov I. Yu., Andronati S. A. Applications of 1-methoxycarbonylmethyl-7-bromo-5-phenyl-3-arylamino-1,2-dihydro-3H-1,4-benzo-diazepin-2-one as an analgesic agent//U.S. Pat. No. 103,803, MPK (2013) CO7D 243/14, 243/26, 243/24, 209/00, application No a 201114668; declared Dec. 12, 2011; publ. 25 Nov. 2013 Bull. No 22; Pavlovsky V. I., Ushakov I. Y., Andronati S. A., Kabanova T. A., Khalimova O. I. 7-bromo-5-phenyl-3-arylamino-1,2-dihydro-3H-1, 4-benzdiazepin-2-ones as analgesic agents//U.S. Pat. No. 105,703, IPC (2014) ML7D 243/14, 243/06, 243/16, 209/00, application No a 2012 13432; declared 26 Nov. 2012; publ. 10 Jun. 2014, Bull. No 11; Pavlovskyi V. I., Semenishyna K. O., Andronati S. A., Kabanova T. A., Khalimova O. I., Reder A. S. Use of 3-alkoxy-1,2-dihydro-3N-1,4-benzdyazepin-2-oniv as a highly active analgesic agent//U.S. Pat. No. 108,246, MPK (2011) CO7D 243/14, 243/26), among which the above mentioned compound 1 showed a high analgesic activity in the "writhing" test carried out by intraperitoneal administration of acetic acid.

The invention is based on the task of expanding the range of application of compound 1 and improving knowledge of the mechanisms of its action.

The problem was solved by experimental study of the antinociceptive action of the test compound 1 on the model of NP in rats and on the model of pain with the participation of central mechanisms, in particular, thermal tail flick test in rats. Based on the available data on the positive response of constant pain to anticonvulsants in the acute and paroxysmal phase and considering structure 1, we performed an evaluation of the anticonvulsant action of the compound on models of pentamethylenetetrazol-induced convulsions and seizures caused by maximal electroshock (MES). We have taken into account the possible side reaction (ulcerogenic effect) of the compound in experimental animals, expressed in the formation of defects in the mucous membrane of the gastrointestinal tract or in provocation of already existing peptic ulcer relapses. The probability of ulcers formation of medicinal origin is especially high during administration of non-steroidal anti-inflammatory drugs in high doses and in combination with their long-term use in the form of tablets.

The task is solved by the study of the Compound (formula 1), as a drug that inhibits neuropathic pain without ulcerogenic effect and possesses an anticonvulsant property.

New discovery in the invention is that Compound 1 inhibits neuropathic pain and some convulsions induced by penthylenetetrazole and maximal electroshock (MES) seizures without the formation of defects in the gastrointestinal mucosa (ulcerogenic effect).

EXAMPLE 1

An evaluation of the antinociceptive action of the test compound (1) on a model of neuropathic pain was carried out on 50 male Wistar rats weighing 270-310 g. The model of neuropathic pain was reproduced by ligation of the sciatic nerve at the level of the upper third of the thigh at the level of the popliteal fossa higher than the site of its trifurcation by *N. tibialis*, N. peroneus and *N. suralis* (see Mironov A. N. et al. Guidelines for conducting preclinical studies of drugs. Part one.—Moscow 2012. p. 197-219). The development of the pathological process lasted 14 days. The degree of hyperalgesia was determined using a dolorimeter (Dolorimeter Baseline, USA) by determining the threshold of pain sensitivity (TPS)—the minimum pressure on the lower surface of the rat's foot $(g/mm^2)$, which caused pain in the animal (vocalization and/or withdrawal of the foot). Each animal was given 5 attempts; the threshold value was taken with such a pressure force, which caused a positive response in at least one attempt. The threshold of pain sensitivity was compared on intact and damaged limbs on day 14 after ligation (pathology without treatment), as well as on the injured limb after 2 hours (peak of action) after the drugs administration. The test compound and the reference drug (ketorolac) were administered intragastrally (as gavage) once at doses of 0.5 and 3 mg/kg. Sciatic nerve ligation in animals caused the development of neuropathic pain syndrome, which manifested itself in behavioral reactions of the rat and lowering the threshold of pain sensitivity by an average of 44-48% (see Table 1). The analgesic effect of Compound 1 compared with ketorolac under the conditions of their intragastral administration on the model of neuropathic pain in rats (M±m, n=10, where n is the number of animals in the experiments) is shown in Table 1.

TABLE 1

| | Threshold of pain sensitivity, g/mm$^2$ | | | | |
|---|---|---|---|---|---|
| Groups | Healthy limb | Damaged limb | Changes in the threshold of pain perception * | 2 hours after compounds administration | Pain perception threshold changes** |
| Control | 392.4 ± 24.0 | 390.7 ± 22.4 | −0.3 ± 0.7% | 392.1 ± 20.5 | +0.59 ± 0.8% |
| Compound 1 0.5 mg/kg | 434.3 ± 13.4 | 223.5 ± 20.1 | −48.4 ± 4.6% | 269.3 ± 19.4 | +23.1 ± 5.9% |
| Ketorolac 0.5 mg/kg | 550.0 ± 19.0 | 287.9 ± 19.85 | −47.3 ± 3.9% | 355.0 ± 19.5 | +24.6 ± 5.2% |
| Compound 1 3 mg/kg | 523.6 ± 28.1 | 295.7 ± 29.9 | −44.3 ± 2.9% | 532.8 ± 47.1 | +82.5 ± 6.1% |
| Ketorolac 3 mg/kg | 547.1 ± 15.1 | 296.4 ± 19.6 | −45.7 ± 3.5% | 501.4 ± 34.9 | +70.1 ± 6.2% |

Notes:
Control-dummy operated animals that received an equal volume of solvents;
* regarding healthy limb;
** regarding pathology before administration of compounds Under these conditions, Compound 1 showed a distinct dose-dependent analgesic effect, as evidenced by the increase in the pain sensitivity threshold after 2 hours of its intragastral administration. At a dose of 0.5 mg/kg, which was $ED_{50}$ (according to preliminary studies), the antinociceptive effect of Compound 1 was on average 23.1% relative to the intact limb. According to this activity, Compound 1 practically does not differ from the equimolar dose of ketorolac (+24.6%).

Increase of Compound 1 dose to 3 mg/kg was accompanied by a significant rise in its antinociceptive activity: the increase in the threshold of pain sensitivity after 2 hours was +82.5%, which was bigger than the similar effect of ketorolac at the same dose (+70.1%).

EXAMPLE 2

Compound 1 in a dose of 0.5 mg/kg on the model of thermal stimulation showed analgesic effect, both after oral and parenteral administration. A more pronounced effect was after parenteral administration (see Table 2). Control: solvent (twin, distilled water, pH-corrector). Results of the study of Compound 1 and ketorolac analgesic effects on the model of thermal stimulation (tail-flick) as degree of pain sensitivity threshold increase in relation to the initial level (%), n=10, are given in Table 2.

TABLE 2

| Compound | 1 hour | 2 hours | 4 hours | 6 hours |
|---|---|---|---|---|
| Compound 1 0.5 mg/kg orally | +13.2 | +22.4 | +21.7 | +8.77 |
| Compound 1 3 mg/kg orally | +60.7 | +83.3 | +65.2 | +39.4 |
| Control | +0.5 | +0.7 | 0 | 0 |
| Compound 1 0.5 mg/kg intraperitoneally | +27.4 | +38.4 | +42.3 | +34.9 |
| Control | +0.2 | +0.5 | +0.3 | +0.7 |
| Ketorolac 0.5 mg/kg orally | +7.5 | +14.6 | +28.6 | +12.1 |
| Ketorolac 3 mg/kg orally | +43.4 | +75.7 | +65.7 | +28.1 |
| Control | 0 | +0.2 | +0.5 | +0.5 |

For both ways of administration, the most pronounced effect was at second hour, that lasted another 2 hours, but with intraperitoneal administration at sixth hour still remained at a rather high level, and when administered intragastrically it decreased significantly.

Ketorolac administered orally at the equimolar dose (0.5 mg/kg), based on the degree of analgesic effect, was compared to that of Compound 1 at fourth and sixth hour.

After oral administration of Compound 1 and ketorolac at a dose of 3 mg/kg (which is $ED_{50}$ according to the literature data for ketorolac), the degree of analgesic effect of the compound exceeded the effect of reference drug both by strength and duration.

EXAMPLE 3

Evaluation of the antinociceptive effect of the test compound (1) on the formalin test model. It is known that the pain response after the subcutaneous formalin injection consists of two phases. The first phase of the formalin test is characterized by acute pain that occurs in response to the injection of a chemical stimulus (lasts about 5 minutes) and is mainly associated with the direct activation of thin non-myelinated C-fibers, most of which transmit pulse from pain receptors. The second phase allows assessing tonic pain; it begins from 10 to 15 minutes after formalin injection and lasts for 40-60 minutes. It is the result of the inflammatory process development in peripheral tissues and changes in the function of the neurons of the dorsal horns of the gray matter of the afferent neurons are located. (see Tjosen A., Berge O., Hunskaar S., Rosland H., Hole K. The formalin test: an evaluation of the method Pain. 1992, 51, p. 5-17). Morphine, codeine, nefopam and orfenadrine—centrally acting analgesics are active in both phases, while non-steroidal and anti-inflammatory (indomethacin, naproxen) and steroidal drugs (dexamethasone, hydrocortisone) inhibit only the second stage of the process. Acetylsalicylic acid and paracetamol show antinociceptive activity in both phases (see Hunskaar S, Hole K. The formalin test in mice: dissociation between inflammatory and non-inflammatory pain. Pain. 1987; 30(1), p. 103-14).

The intensity of the pain response in the first (painful) and second (inflammatory) phase of the test was assessed by the duration of the licking patterns (in seconds) which is typical behavioral mice reaction for this test. Reducing the duration of the licking patterns is considered as the presence of an analgesic effect in the tested objects.

The formalin test was carried out on white male non-linear mice weighing 20-24 g. The studied compounds and the reference drug—diclofenac-sodium, which has a biphasic effect in the mice model (see Zhi-Yu Yin, Lu Li, Shuai-Shuai Chu, Qing Sun, Zheng-Liang Ma, Xiao-Ping Gu•Antinociceptive effects of dehydrocorydaline in mouse models of inflammatory pain involve the opioid receptor and inflammatory cytokines. Sci Rep. 2016, 6, p. 1-9) were administered intraperitoneally 40 minutes prior the inflammation induction. A control group of mice received an equivalent amount of physiological solution in Tween-80 emulsion. The edema formation was induced by an intraplantar injection of a 0.01 ml 3% aqueous formalin solution with a micro syringe (20 µl) into the right hind paw of the experimental and control animals.

Each experimental animal was observed for 40 minutes, controlling the time spent by the animal for licking the injured paw. The intensity of the pain response in the first and second phases of the test was assessed with the number and duration of the licking patterns (in seconds) of the injected paws. The licking time was summed up for each animal. The ability of the studied compounds to influence the pain behavior of the experimental animals in the first (painful) phase (0-5 min) and the second (inflammatory) phase (15-40 min) was determined by decreasing the time of licking of the injured paw (see The formalin test: an evaluation of the method/A. Tjolsen, O.-G. Berge, S. Hunskaar [et al.]//Pain.—1992.—Vol. 51.—P. 5-17).

The effect of Compound 1 on the pain behavior of mice in the formalin test is presented in Table 3.

TABLE 3

| | Dosage, mg/kg | I phase, % effect (decrease in the time of licking of the paw) | II phase, effect (decrease in the time of licking of the paw) |
|---|---|---|---|
| Compound 1 | 3.00 | 91.10 ± 18.80*** | 98.4 ± 15.0*** |
| | 0.10 | 76.00 ± 6.50*** | 54.00 ± 8.60*** |
| | 0.01 | 15.00 ± 4.11 | 32.10 ± 10.10** |
| Diclofenac-sodium | 10.00 | 51.00 ± 11.64*** | 53.60 ± 11.02*** |

Reliability relative to control at
** $p \leq 0.01$ with regard to control;
*** $p \leq 0.001$ with regard to control.

In a dose of 0.1 mg/kg, Compound 1 in the first phase of the test was 1.5 times more active than diclofenac sodium, administered at a dose of 10 mg/kg, and comparable to it in the second phase.

The effect of Compound 1 was tested in a formalin test under its administration in the range from 0.01 mg/kg to 3.0 mg/kg. The results of the experiments demonstrate its ability to reduce the animal's painful behavior in both the first (painful) and second (inflammatory) phases. Moreover, in both cases, the dose-dependent nature of the action of the compound is observed. Thus, the experimental data obtained on the basis of the formalin test demonstrate the presence of significant analgesic and anti-inflammatory activity in Compound 1.

EXAMPLE 4

Given the fact that Compound 1 affects not only the painful, but also the inflammatory phase, we undertook an in-depth study of its anti-inflammatory effect. The most common screening method of anti-inflammatory activity is the model of inflammatory edema of the rat hind paw, induced by the subplantar administration of various phlogogenic agents. Under the conditions of carrageenan administration, a sufficiently pronounced edema reaction is observed, which slowly develops and persists for a long time. The maximum size of edema is observed in 2-4 hours. Compounds that exhibit anti-inflammatory and anti-exudative properties inhibit the development of inflammatory reactions and reduce the size of edema and hyperemia of the tissue.

The anti-inflammatory properties of the test compounds were studied in the model of carrageenan rat paw edema. Male white rats weighing 150-180 g were used in the experiments. Before the administration of the experimental substances, the volumes of the rats' paws subsequently injected by phlogogen were measured. The test compounds and the reference drug—diclofenac-sodium, were administered intraperitoneally 40 minutes prior the inflammation induction. The control group of the rats received an equivalent amount of physiological solution in the emulsion with Tween-80. Acute aseptic inflammation was induced by a 1% aqueous solution of 0.1 ml)—carrageenan injection under plantar aponeurosis of the hind paw of animals of the experimental and control groups (see Trinus F. P. Nonsteroidal anti-inflammatory drugs/F. P. Trinus, N. A. Mohort, B. M. Klebanov//K., 1975, pp. 204-231., Winter C. A. Carrageenin—induced edema in hind paw of the rat as an assay for antiinflammatory drugs/C. A. Winter, E. A. Risley, G. V. Nuss//Proc. Soc. Exp. Biol. Med.—1962.—Vol. 111.—P. 544-547). The inflammatory reaction significance was evaluated after two and four hours after the phlogogen injection. Registration of edema size was carried out by mechanical measurement of foot volume in dynamics according to Zakharevsky A. S. (see Zaharevskiy A. S. The influence of some indole derivatives on the nervous system. Diss. cand. med. science/Zaharevskiy Aleksandr Stepanovich-Minsk.—1969.—78-80 p.). The edema extent was estimated according to the difference in volume between the swollen paw and the paw before inflammation induction. The anti-inflammatory efficacy of the test compounds was determined as the ability of the test compounds to suppress the inflammatory response in the experimental animals compared to the control animals and expressed as a percentage. The calculation was carried out according to the following formula:

The percentage of inflammation suppression= $(\Delta V_\kappa - \Delta V_\pi / \Delta V_\kappa) \cdot 100\%$, where: $\Delta V_\kappa$—the average increase in the volume of the swollen paw in the control;

$\Delta V_\pi$ —the average increase in the volume of the swollen paw in animals injected by experimental substances.

The anti-inflammatory activity of Compound 1 on the rat paw inflammatory edema model caused by the subplantar administration of carrageenan is presented in Table 4.

TABLE 4

| | Dosage, mg/kg | Inhibition of edema in 2 hours (%) | Inhibition of edema in 4 hours (%) |
|---|---|---|---|
| Compound 1 | 3.0 | 36.7 ± 4.1** | 25.00 ± 2.7* |
| | 10.0 | 47.0 ± 4.1*** | 26.70 ± 5.4* |
| Diclofenac-sodium | 10.0 | 43.0 ± 7.0*** | 57.10 ± 8.3*** |

Reliability relative to control at
*$p < 0.05$ with regard to control
** $p \leq 0.01$ with regard to control;
***$p \leq 0.001$ with regard to control.

Studies have shown that Compound 1 moderately reduced the size of the edema at a dose of 3 mg/kg. An increase in the dose of Compound 1 to 10 mg/kg resulted in a decrease in the volume of edema compared to diclofenac sodium effect in 2 hours; inhibition of the exudative reaction in 4 hours was somewhat lower.

EXAMPLE 5

In many cases, the presence of anticonvulsant (antiepileptic) effect of the compounds correlates with analgesic properties on corresponding models of neuralgia. As a general step is a primary screening of new anticonvulsant compounds on rodents with the help of pentylenetetrazole test and MES (maximal electroshock seizures) as they have a qualitative difference in development and manifestations of seizures. It is believed that the compound ability to prevent the MES-induced seizures is connected with impulse spread inhibition throughout the central nervous system. It is believed that the ability to prevent the MES-induced seizures development indicates the potential efficacy of the compound in the preventing propagation of a pulse along the neural tissue (see Tompson E. Medicines. Bioscreening/Under the editorship of A. V. Stefanova.-K.: Avitsenna, 1998.—250 p.).

The experiments were performed on non-linear male mice weighing 19-29 g. Pentylenetetrazole was administered subcutaneously in the cervical region of the back. Based on the physico-chemical properties of pentylenetetrazole, the shape of the curve which characterizes "dose-effect" relationship of this seizure agent was first defined. In our case, the value $ED_{95}$ of pentylenetetrazole (Sigma) was of 120 mg/kg. The animals were observed within 30-60 min after the pentylenetetrazole injection with the registration of the main index—primary generalized clonic seizures, accompanied by loss of the overturning reflex.

For MES-induced seizures experimental animals were exposed to electric stimulation through the corneal electrodes (50 Hz, 50 mA for mice during 0.2 s). The number of animals with the maximum tonic extension of the hind limbs, which occurs in almost 100% of the animals in the control group, was calculated. For the statistically significant determination of $ED_{50}$, 3 doses of the test compound were used; the effect of each dose was studied in 6-8 animals.

As reference preparations for this model gabapentin and pregabalin were chosen, these ones are effective during post-operative use of anesthesia and cancer-associated neuropathic pain. These preparations are not effective in the treatment of HIV-associated sensory neuropathy. In some countries, the preparations are approved for the treatment of partial epileptic seizures and mixed convulsive disorders, but there is not enough data on their use in generalized epilepsy (see Huppertz H J, Feuerstein T J, Schulze-Bonhage A Myoclonus in epilepsy patients with anticonvulsive add-on therapy with pregabalin. Epilepsia 2001 42:790-792; Mathew N T, Rapoport A, Saper J, Magnus L, Klapper J, Ramadan N, Stacey B, Tepper S: Efficacy of gabapentin in migraine prophylaxis. Headache. 2001 February; 41(2):119-28).

The anticonvulsive activities of Compound 1 and reference preparations are given in Table 5.

TABLE 5

| Compound 1 | Gabapentin | Pregabalin |
|---|---|---|
| Pentylenetetrazole 0.91 (0.83-0.97) mg/kg | 32 (50-200) mg/kg | 31 (16-62) mg/kg |
| MES 8.2 (6-11) mg/kg | 19 (16-24) mg/kg | 73 (57-93) mg/kg |

Note:
Data regarding gabapentin and pregabalin were obtained from the following literature sources (see Akula KK, Dhir A, Kulkarni SK. Effect of various antiepileptic drugs in a pentylenetetrazol-induced seizure model in mice. Methods Find Exp Clin Pharmacol. 2009, 31(7), pp. 423-32.; Mark G. Vartanian, Louis L. Radulovic, Jack J. Kinsora, Kevin A. Serpa, Marguerite Vergnes, Edward Bertram, Charles P. Taylor. Activity profile of pregabalin in rodent models of epilepsy and ataxia. Epilepsy Research. 2006, 68 pp. 189-205).

Note: Data regarding gabapentin and pregabalin were obtained from the following literature sources (see Akula K K, Dhir A, Kulkarni S K. Effect of various antiepileptic drugs in a pentylenetetrazol-induced seizure model in mice. Methods Find Exp Clin Pharmacol. 2009, 31(7), pp. 423-32; Mark G. Vartanian, Louis L. Radulovic, Jack J. Kinsora, Kevin A. Serpa, Marguerite Vergnes, Edward Bertram, Charles P. Taylor. Activity profile of pregabalin in rodent models of epilepsy and ataxia. Epilepsy Research. 2006, 68 pp. 189-205).

The data in Table 5 indicate that Compound 1 is more effective than gabapentin and pregabalin in the used experimental models.

EXAMPLE 6

The disadvantage of most analgesics is the fact that they have ulcerogenic effect that interferes with their long-term use. We have studied this side effect of Compound 1 in acute and subchronic experiments. In the first scheme, the compound in the form of an aqueous suspension (Tween-80) was administered in single dose intragastrically to rats, which had previously been deprived of food for 16 hours with free access to water. After 3 hours, the animals were euthanized with a cervical dislocation, then, after dissection of the abdominal cavity, stomachs were ejected and washed in isotonic sodium chloride solution to take out the contents. Damage of stomach was determined visually. In the second scheme, the compound was administered intragastrically for 4 days, after that the extent of the damaging effect on the stomach was determined, as in the previous experiment.

Evaluation of ulcerogenic action was carried out on a 4-score scale:

0 score—no damage; 0.5 score—hyperemia (blood vessels overflow)

1 score—single minor lesions (1-3 point hemorrhages or small ulcers)

2 score—multiple (more than 3) lesions (erosions, pinpoint hemorrhages) or 1 large ulcer 3 score—significant and massive damages (erosions, hemorrhages) of the gastric mucosa with significant size (diameter up to 4 mm)

4 score—gross injuries (massive hemorrhages, erosions, perforations) that cover the entire surface of the gastric mucosa.

The average multiplicity index of damage to the gastric mucosa (the number of ulcers per animal) and the severity of the damage (in scores) were determined.

Compound 1 was administered over a wide dose range—in acute studies—50, 250, 500 and 1000 mg/kg. For the subchronic experiment, the compound was used at a dose of 50 mg/kg.

Control animals received equivalent amounts of solvent.

To determine the safety of this compound in a chronic trial during long-term administration, it was administered to rats for 28 days at a dose close to $ED_{50}$ by analgesic effect (0.5 mg/kg).

The results of studies of the ulcerogenic effect of Compound 1 in the acute experiment are shown in Table 6. They showed that the administration of the test compound in a dose-dependent manner caused single minor damages of the gastric mucosa, mainly in the form of erosions and spot hemorrhages. The severity of the lesion corresponded to score 1, but in individual animals—to score 2. No animals with heavier lesions of the gastric mucosa were detected. The maximum average score for damage of the gastric mucosa was noted at a dose of 1000 mg/kg and was of 1.3±0.21. The further dose increase wasn't made by reason of the impossibility to obtain proper suspension. So, it was not possible to calculate the value of $ED_{50}$.

TABLE 6

| Dose, mg/kg | Number of animals with lesions of the gastric mucosa of different extent | | | | Average score | Multiplicity of damage |
|---|---|---|---|---|---|---|
| | score 1 | score 2 | score 3 | score 4 | | |
| 50 mg/kg | 3 | 0 | 0 | 0 | 0.2 ± 0.13 | 0.5 ± 0.34 |
| 250 mg/kg | 5 | 2 | 0 | 0 | 0.8 ± 0.25 | 0.9 ± 0.31 |
| 500 mg/kg | 7 | 3 | 0 | 0 | 1.0 ± 0.21 | 1.2 ± 0.25 |
| 1000 mg/kg | 8 | 3 | 0 | 0 | 1.3 ± 0.21 | 2.0 ± 0.37 |
| Control | 0 | 0 | 0 | 0 | 0 | 0 |

Thus, our data showed the absence of damaging effect of Compound 1 on the gastric mucosa under the given experimental conditions.

We also determined the indexes of gastrotoxicity of gastric mucosa under conditions of repeated intragastral administration (for 4 days at a dose of 50 mg/kg). In a macroscopic examination of the gastric mucosa, an insignificant decrease in the folding of the gastric mucosa and a rather distinct decrease in the amount of mucus were noticed. Evaluation of the ulcerogenic effect of Compound 1 in the subchronic experiment (n=10) is shown in Table 7. Counting the number and extention of lesions, the results of which are presented in the table, showed that, as in the acute experiment, the lesions of the gastric mucosa in animals corresponded to scores 1-2, deeper or widespread lesions were not revealed. The average severity in this group was of 1.4±0.27 score, and the multiplicity was of 1.9±0.64 ulcers per animal. This also indicates the absence of a gastrotoxic effect of this compound on the stomach.

TABLE 7

| | score 1 | score 2 | score 3 | score 4 | | |
|---|---|---|---|---|---|---|
| 50 mg/kg | 6 | 5 | 0 | 0 | 1.4 ± 0.27 | 1.9 ± 0.64 |
| Control | 0 | 0 | 0 | 0 | 0 | 0 |

The data presented indicate that there is no serious damage to the stomach from the test compound, even when administered at very high doses, several orders higher than the average effective doses, and which are close to the upper limit of permitted doses that can be administered to rats once. Therefore, at the next stage it became reasonable to determine the effect of Compound 1 on the stomach after prolonged use (28 days) in an average effective dose of 0.5 mg/kg. Assessment of the ulcerogenic effect of Compound 1 (0.5 mg/kg) in the chronic experiment is presented in Table 8.

TABLE 8

| Dose, mg/kg | Number of animals with different degrees lesions of the gastric mucosa | | | | Average score | The multiplicity of damage |
|---|---|---|---|---|---|---|
| | score 1 | score 2 | score 3 | score 4 | | |
| 0.5 mg/kg (n = 14) | 4 | 1 | 0 | 0 | 0.4 ± 0.17 | 0.5 ± 0.23 |
| Control (n = 10) | 0 | 0 | 0 | 0 | 0 | 0 |

The results showed that the 28-day intragastral administration of Compound 1 at an average effective dose of 0.5 mg/kg had no negative effect on the gastric mucosa. Of the 14 animals in the experimental group, only in 4 were observed single superficial injuries, which can be estimated as score 1. In one rat ulcer with score 2 was detected. In this group, the multiplicity of lesions was 0.5±0.23, and the mean score was 0.4±0.17.

The invention claimed is:

1. A method for treating neuropathic pain in a subject in need thereof, the method comprising administering to the subject a therapeutically effective amount of the compound of formula (I):

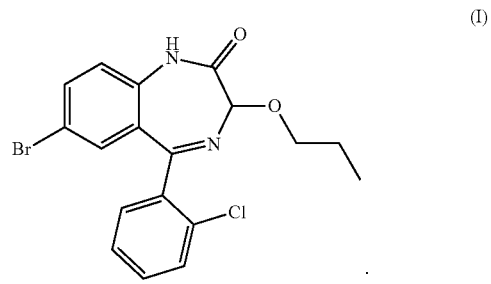 [SMILES: CCCOC1N=C(c2ccccc2Cl)c2cc(Br)ccc2NC1=O]

(I)

2. The method of claim 1, further comprising mitigating a side effect of an ulcerogenic event in the subject.

3. The method of claim 1, wherein the neuropathic pain is caused by diabetes mellitus, herpetic infection, stroke, multiple sclerosis, malignant diseases, HIV infection, or post-traumatic or postoperative damage to the peripheral nervous system.

4. The method of claim 1, wherein the therapeutically effective amount of the compound of formula (I) is administered orally or intraperitoneally.

* * * * *